(12) United States Patent
Lee et al.

(10) Patent No.: US 9,102,706 B2
(45) Date of Patent: Aug. 11, 2015

(54) NEWLY IDENTIFIED COLON CANCER MARKER AND DIAGNOSTIC KIT USING THE SAME

(71) Applicant: INDUSTRY FOUNDATION OF CHONNAM NATIONAL UNIVERSITY, Gwangju (KR)

(72) Inventors: Tae Hoon Lee, Gwangju (KR); Hee Young Yang, Daegu (KR); Joseph Kwon, Jeonju-si (KR); Kyoung Jin Chung, Gwangju (KR); Young Kyu Park, JHwasun-gun (KR)

(73) Assignee: Industry Foundation of Chonnam National University, Gwangju (KR)

( * ) Notice: Subject to any disclaimer, the term of this patent is extended or adjusted under 35 U.S.C. 154(b) by 184 days.

(21) Appl. No.: 13/643,221

(22) PCT Filed: Oct. 17, 2012

(86) PCT No.: PCT/KR2012/008459
§ 371 (c)(1),
(2) Date: Dec. 12, 2012

(87) PCT Pub. No.: WO2013/062261
PCT Pub. Date: May 2, 2013

(65) Prior Publication Data
US 2013/0137603 A1 May 30, 2013

(30) Foreign Application Priority Data

Oct. 28, 2011 (KR) .................. 10-2011-0110848

(51) Int. Cl.
| | |
|---|---|
| *C07K 16/00* | (2006.01) |
| *G01N 33/53* | (2006.01) |
| *G01N 33/574* | (2006.01) |
| *C07K 7/08* | (2006.01) |
| *C07K 7/06* | (2006.01) |
| *C07K 16/18* | (2006.01) |
| *C12Q 1/68* | (2006.01) |
| *G01N 33/68* | (2006.01) |

(52) U.S. Cl.
CPC ... *C07K 7/08* (2013.01); *C07K 7/06* (2013.01); *C07K 16/18* (2013.01); *C12Q 1/6886* (2013.01); *G01N 33/57419* (2013.01); *G01N 33/6893* (2013.01); *C12Q 2600/158* (2013.01); *G01N 2033/57465* (2013.01)

(58) Field of Classification Search
CPC ............. A61K 39/39558; C07K 16/28; C07K 16/3046
See application file for complete search history.

(56) References Cited

U.S. PATENT DOCUMENTS

| | | | |
|---|---|---|---|
| 2006/0257857 A1* | 11/2006 | Keene et al. | 435/5 |
| 2007/0128598 A1* | 6/2007 | Boender | 435/6 |

FOREIGN PATENT DOCUMENTS

| | | | |
|---|---|---|---|
| KR | 1020110088462 A | | 8/2011 |
| WO | WO 2007027957 A2 * | | 3/2007 |

OTHER PUBLICATIONS

Armstrong et al., Recent Results Cancer Res. 2005: 166:99-112.*
Tockman et al., Cancer Res. 1992, 52: 2711s-2718s.*
Korean Intellectual Property Office, Office Action dated Jun. 3, 2014, issued in corresponding Application No. 10-2011-0110848.
Hernandez, et al., "Assessment of Differential Gene Expression Patterns in Human Colon Cancers", Annals of Surgery, vol. 232, No. 4, p. 576-585.
GenBank Accession No. GQ372827.1, Ovis aries keratin 5 (KRT5) mRNA, partial CDs, Aug. 19, 2009.
GenBank Accession No. ACU45490.1, keratin 5 [Ovis aries], Aug. 19, 2009.
Matthias Futschik et al., "Gene Expression Profiling of Metastatic and Nonmetastatic Colorectal Cancer Cell Lines", Genome Letters 2002, 2002, vol. 1, No. 1, pp. 26-34.
Gennadi V. Glinsky et al., "Common malignancy-associated regions of transcriptional activation (MARTA) in human prostate, breast, ovarian, and colon cancers are targets for DNA amplification", Cancer Letters, Elsevier Ireland Ltd., Nov. 10, 2003, vol. 201, Issue 1, pp. 67-77.
Choi et al., "Proteomic Analysis of Microvesicles Derived from Human Colorectal Cancer Cells", Journal of Proteome Research, Dec. 2007, vol. 6, No. 12, pp. 4646-4655.
International Searching Authority, International Search Report dated Jul. 1, 2013, issued in corresponding Application No. PCT/KR2012/008459.

* cited by examiner

*Primary Examiner* — Hong Sang
(74) *Attorney, Agent, or Firm* — Sughrue Mion, PLLC

(57) ABSTRACT

Provided are a newly identified colon cancer marker and a diagnostic kit using the same. More particularly, the present invention relates to an identified colon cancer specific marker, a composition and a kit including agents determining presence of the marker, and a method of diagnosing colon cancer using the same. The diagnostic marker according to the present invention capable of detecting metastasis and prognosis of colon cancer may provide useful information for the treatment and management of colon cancer and be used for the development of colon cancer-specific anticancer agents.

5 Claims, 6 Drawing Sheets
(1 of 6 Drawing Sheet(s) Filed in Color)

```
                              SEQUENCE LISTING

<160> NUMBER OF SEQ ID NOS: 8

<210> SEQ ID NO 1
    <211> LENGTH: 15
    <212> TYPE: PRT
    <213> ORGANISM: Artificial Sequence
    <220> FEATURE:
    <223> OTHER INFORMATION: Synthetic construct of KRT5 peptide

<400> SEQUENCE: 1

Asn Lys Tyr Glu Asp Glu Ile Asn Lys Arg Thr Thr Ala Glu Asn
    1               5                   10                  15

<210> SEQ ID NO 2
    <211> LENGTH: 10
    <212> TYPE: PRT
    <213> ORGANISM: Artificial Sequence
    <220> FEATURE:
    <223> OTHER INFORMATION: Synthetic construct of TUBB peptide

<400> SEQUENCE: 2

Asp Phe Gly Glu Glu Ala Glu Gly Glu Ala
    1               5                   10

<210> SEQ ID NO 3
    <211> LENGTH: 15
    <212> TYPE: PRT
    <213> ORGANISM: Artificial Sequence
    <220> FEATURE:
    <223> OTHER INFORMATION: Synthetic construct of COL6A1 peptide

<400> SEQUENCE: 3

Cys Ser Phe Glu Cys Gln Pro Ala Arg Gly Pro Pro Gly Leu Arg
    1               5                   10                  15

<210> SEQ ID NO 4
    <211> LENGTH: 15
    <212> TYPE: PRT
    <213> ORGANISM: Artificial Sequence
    <220> FEATURE:
    <223> OTHER INFORMATION: Synthetic construct of JUP peptide

<400> SEQUENCE: 4

Phe Arg Ile Ser Glu Asp Lys Asn Pro Asp Tyr Arg Lys Arg Val
    1               5                   10                  15

<210> SEQ ID NO 5
    <211> LENGTH: 45
    <212> TYPE: DNA
    <213> ORGANISM: Artificial Sequence
    <220> FEATURE:
```

```
<223> OTHER INFORMATION: Synthetic construct of nucleotide encoding KRT5
      peptide

<400> SEQUENCE: 5
aacaagtatg aggatgaaat caacaagcgt accactgctg agaat            45

<210> SEQ ID NO 6
<211> LENGTH: 30
<212> TYPE: DNA
<213> ORGANISM: Artificial Sequence
<220> FEATURE:
<223> OTHER INFORMATION: Synthetic construct of nucleotide encoding TUBB
      peptide

<400> SEQUENCE: 6
gatttcggtg aggaggccga agaggaggcc                             30

<210> SEQ ID NO 7
<211> LENGTH: 45
<212> TYPE: DNA
<213> ORGANISM: Artificial Sequence
<220> FEATURE:
<223> OTHER INFORMATION: Synthetic construct of nucleotide encoding
      COL6A1 peptide

<400> SEQUENCE: 7
tgctccttcg aatgccagcc tgcaagagga cctccggggc tccgg            45

<210> SEQ ID NO 8
<211> LENGTH: 45
<212> TYPE: DNA
<213> ORGANISM: Artificial Sequence
<220> FEATURE:
<223> OTHER INFORMATION: Synthetic construct of nucleotide encoding JUP
      peptide

<400> SEQUENCE: 8
ttccgcatct ccgaggacaa gaacccagac taccggaagc gcgtg            45
```

NEWLY IDENTIFIED COLON CANCER MARKER AND DIAGNOSTIC KIT USING THE SAME

CROSS REFERENCE TO RELATED APPLICATIONS

This application is a National Stage of International Application No. PCT/KR2012/008459 filed Oct. 17, 2012, claiming priority based on Korean Patent Application No. 10-2011-0110848 filed Oct. 28, 2011, the contents of all of which are incorporated herein by reference in their entirety.

TECHNICAL FIELD

The present invention relates to a newly identified colon cancer marker and a diagnostic kit using the same. More particularly, the present invention relates to an identified colon cancer specific marker, a composition and a kit including agents determining the presence of the marker, and a method of diagnosing colon cancer using the same.

BACKGROUND ART

Unlike a normal cell of which division and proliferation are well-controlled according to needs of an individual, cancer commonly means diseases that form many abnormal cells through unrestrained division and proliferation due to mutation caused by several carcinogenetic factors and changes in the intercellular environment in genes related to cell growth to invade the surrounding tissue and organs, thereby causing neoplasia and destruction of the normal tissue (Lopez A. D., et al., Lancet, 367:1747-1757, 2006).

Colon cancer, which is one of the carcinomas and includes rectal cancer, colon cancer, and anal cancer, shows high mortality rate in the United States, which is a representative of a developed country (Shike M, et al., Bull World Health Organ, 68: 377-385, 1990; UK Bowel Cancer Incidence Statistics, at info.cancerresearchuk.org/cancerstats/types/bowel/incidence, last visited Apr. 24, 2009.

Symptoms of colon cancer are not specific to only large intestine. Therefore, it may be difficult to assert which symptom is a characteristic symptom indicating colon cancer. However, generally, colon cancer patients have symptoms such as a change in bowel habits, bloody stool or mucous stool (mucous is mixed in stool), thinner stool, weight loss, abdominal discomfort (abdominal pain, abdominal distension), fatigue, loss of appetite, vomiting, nausea, anemia, or the like. Such as all of the cancer, in the case of colon cancer, when it is detected early and appropriately treated, colon cancer may also be completely cured.

However, most colon cancers do not show any symptom during early stage of colon cancer, and in the case in which some symptom appears due to colon cancer, generally, colon cancer has already significantly progressed. The reason is that in the early stage of colon cancer, a size of cancer is small and no symptoms appear, but in the case in which the cancer grows and the size thereof becomes large, the cancer blocks the stool from passing in the large intestine, bleeding occurs in the growing colon cancer, and secretion is secreted from the surface of colon cancer. As a colon cancer screening test currently used, there are a fecal occult blood test, a tumor marker test, a barium enema, a colonoscopy, a computed tomography (CT), an abdomen ultrasonography, a transrectal ultrasonography, and a sigmoidoscopy test, but these tests have several limitations in the early diagnosis. Considering that a survival rate for stage 1 is 90% or more but a survival rate for stage 4 in which the cancer has already spread to distant organs such as the lung, liver, or the like, drops to below 5%, in order to improve the survival rate of colon cancer patients, a method of more accurately and detecting early colon cancer needs to be developed. To this end, a diagnostic system capable of improving accuracy is required, which requires identification of colon cancer-related marker genes. In addition, in the case of colon cancer development, the colon cancer marker may be appropriately used to predict prognosis and determine treatment strategy.

It is known that changes in various genes such as various kinds of oncogenes, tumor suppressor genes, and the like, are involved in the process of the carcinogenesis of colon cancer. Actually, colon cancer is cancer of which genetic changes occurring in the process of carcinogenesis have been well identified. In colon cancer, a change in a single oncogene or tumor suppressor gene may not cause cancer alone. When normal large intestinal epithelium progresses to colon cancer through an adenoma stage, changes in various cancer-related genes need to be accumulated over a long period of time, that is, over several years, which is called multistage changes in genes in the carcinogenesis of colon cancer. Here, the important thing is not a change sequence of genes at each stage but the total sum of changes ultimately accumulated in the genes. Examples of genetic changes involved in the carcinogenesis of colon cancer include K-ras gene mutations, adenomatous polyphosis coili (APC) gene mutations, mutated in colon cancer (MCC) gene mutations, deleted in colon cancer (DCC) gene on chromosome 18, p53 gene mutations on chromosome 17, and deoxyribonucleic acid (DNA) methylation disorder, and the like, and mutations in human Mut S homologue 2 (hMSH2) gene, hMSH1 gene, human post-meiotic segregation 1 (hPMS1) gene, hPMS2 gene are involved therein.

The European Group on Tumor Markers (EGTM) guidelines for clinical use of markers in colon cancer was reported by European researchers in 2003 (Duffy M. J., et al., Eur. J Cancer 39: 718-727, 2003). This guideline individually focuses on carcinoembryonic antigen (CEA), which is a serum marker. In addition to the CEA, carbohydrate antigen 19.9 (CA19.9), CA 242, tissue inhibitor of metalloproteinase type 1 (TIMP-1), Ras, p53, thymidylate synthase (TS), Musashi (MSI), DCC, or the like, have been suggested as the marker, and the evidences have been proven, but cancer-specific characteristics are still not founded therein (Duffy M. J., et al., Eur. J. Cancer 43:1348-1360, 2007).

As described above, since development of the carcinogenesis is complexly related to various genes, expression of these genes, and a mechanism of regulation thereof, researches into a technology of identifying a marker for new diagnosis and treatment of the cancer by comparing expression rates of cancer-related genes using an oligo-chip using a large amount of genes have been recently conducted. Genes of which expression increases or decreases in cancer cells are involved in various processes such as cell division, cell signaling, cytoskeleton, cell movement, cell defense, gene and protein expression, intracellular metabolism in cancer cells, and the like. There are some genes having the same expression changes as that of each patient, but there are many genes having different expression changes according to the patient's tissue. Specificity of each patent may be the most likely reason. Therefore, accurate pathological findings and classification for the tissue of the studied target patient has been required, and detection and identification of new genes has been further required for more accurate diagnosis using genes.

DISCLOSURE

Technical Problem

The present inventors researched into finding proteins related to colon cancer and identified proteins showing an expression change specific to the colon cancer tissue, thereby completing the present invention by confirming that the proteins may be usefully used as a marker for diagnosing colon cancer.

An object of the present invention is to provide polypeptides for diagnosing early colon cancer using protein expression patterns of tissue of colon cancer patient.

Another object of the present invention is to provide a composition for detecting a cancer marker including an agent capable of detecting expression of proteins that is specifically expressed in the tissue of the colon cancer patient.

Another object of the present invention is to provide a diagnostic kit for detecting a cancer marker including the composition for detecting cancer marker.

Technical Solution

In one general aspect, there are provided an identified colon cancer specific marker, a composition and a kit including agents measuring presence of the marker, and a method of diagnosing colon cancer using the same.

Hereinafter, the present invention will be described in detail.

According to the present invention, there are provided polypeptides for diagnosing early colon cancer using protein expression patterns of the tissue of the colon cancer patient, and polynucleotides encoding the polypeptide.

More specifically, the present invention provides colon cancer marker polypeptides including an amino acid sequence encoding proteins encoded by polynucleotide sequences of SEQ ID NOS: 5 to 8, and polypeptide fragments inducing production of antibodies to the colon cancer marker polypeptides.

The polypeptide may be a polypeptide represented by an amino acid sequence selected from a group consisting of SEQ ID NOS: 1 to 4.

The amino acid sequence selected from the group consisting of SEQ ID NOS: 1 to 4 may be encoded by polynucleotide selected from a group consisting of base sequences of SEQ ID NOS: 5 to 8.

In the present invention, the term "diagnosis" means confirming a presence or features of pathological states. With respect to the objects of the present invention, the terms "diagnosis" is to determine the incidence of colon cancer.

In the present invention, the term "colon cancer" means a cancer generated in a mucosa, which is the innermost surface of the large intestine, and includes rectal cancer, colon cancer, and anal cancer.

In the present invention, the term "diagnostic marker", "marker for diagnosis", or "diagnosis marker" means a substance capable of being used to distinguish colon cancer cells from normal cells and diagnose colon cancer and includes organic biomolecules of which quantities are increased or decreased in the colon cancer cells as compared to the normal cells, such as polypeptides or nucleic acids (for example, messenger ribonucleic acid (mRNA), etc.), lipids, glycolipids, glyco-proteins, sugars (monosaccharide, disaccharide, oligosaccharide, etc.), or the like. With respect to the objects of the present invention, the colon cancer diagnosis marker may be at least one protein selected from a group consisting of KRT5, TUBB, COL6A1, and JUP and show an expression change specific the colon cancer cell.

Selection and application of a significant diagnosis marker may determine reliability of diagnosis results. The significant diagnosis marker means a marker having high validity so that results obtained by diagnosis may be accurate and having high reliability so that the same result may be obtained even at the time of repetitive measurements. The colon cancer markers according to the present invention are highly reliable markers, which are proteins always showing expression changes due to direct and indirect factors according to development of colon cancer, having high reliability due to great differences in expression levels as compared with the control group, thus having low or no possibility of obtaining false results. Therefore, the diagnosis based on the results obtained by measuring an expression degree of the significant diagnosis marker may be reasonably reliable.

Here, proteins having an expression changes 2 times larger in the colon cancer tissue than that of proteins expressed in the normal tissue used as the control group was identified using a relative quantitative analysis method (nano-ultra performance liquid chromatography mass spectrometry (nano-UPLC-MS)) among overlapping 83 proteins between 168 proteins identified in normal colon tissues and 225 proteins identified in colon cancer tissues.

In Another general aspect, there is provided a composition for detecting a cancer marker including the agent capable of detecting expression of proteins that is specifically expressed in the tissue of the colon cancer patient.

More specifically, there is provided the composition for detecting colon cancer, including an agent measuring expression or protein levels of one or more genes selected from KRT5 (GenBank No. NM_000424, keratin 5), TUBB (GenBank No. NM_178014 tubulin, beta class I), COL6A1 (GenBank No. NM_001848, collagen, type VI, alpha 1), and JUP (GenBank No. NM_002230, junction plakoglobin).

The agent may be antibodies specifically binding to polypeptides represented by at least one amino acid sequence selected from a group consisting of sequence numbers 1 to 4, or combinations thereof; or a pair of primer, a probe, or anti-sense nucleotides that are specifically binding to at least one polynucleotide having the base sequence selected from a group consisting of sequence numbers 5 to 8.

In the present invention, the term "primer" means a short nucleic acid sequence having the free 3'—OH group, which forms a base-pair with a complementary template and serves as a starting point for template strand replication.

The primer may initiate DNA synthesis in the presence of four different nucleoside triphosphates and an agent for polymerization (that is, DNA polymerase or reverse transcriptase) in an appropriate buffer and at a suitable temperature. The primer of the present invention, which is a primer specific to each of the marker genes, may be sense and anti-sense nucleic acids having sequences of 7 to 50 nucleotides. And also, the primer of the present invention may be used as additional features as well as the basic properties of the primer acting as the starting point of DNA synthesis are not changed.

The primer of the present invention may be chemically synthesized by a phosphoramidite solid support method or other well-known methods. This nucleic acid sequence may also be deformed by the known methods in the art. Nonrestrictive examples of this deformation may include methylation, capping, substitution to analogues of at least one natural nucleotide, and deformation between nucleotides, for example, deformation into an uncharged connector (for example, methyl phosphonate, phosphotriester, phosphoramidate, carbamate, or the like) or a charged connector (for example, phosphorothioate, phosphorodithioate, or the like). The nucleic acid may contain at least one additional covalently bonded residue, for example, proteins (for example, nuclease, toxin, antibody, signal peptide, poly-L-lysine, or the like), an insert material (acridine, psoralene, or the like), a chelating agent (for example, a metal, a radioactive metal, iron, an oxidative metal, or the like), and alkylating agent. The nucleic acid sequence of the present invention may also deformed using a marker capable of directly or indirectly providing a detectable signal. Examples of the marker include a radioactive isotope, a fluorescent molecule, biotin, and the like.

In the present invention, the term "measurement of the protein expression level" means a process of confirming whether or not the protein expressed from the colon cancer marker genes is present in a biological sample and an expression degree thereof in order to diagnose colon cancer. Preferably, an amount of proteins may be confirmed using the antibody specifically binding to the protein of the gene. Analysis methods for measuring protein levels include a western blotting method, an enzyme linked immunosorbent assay (ELISA) method, a radioimmunoassay (RIA) method, a radioimmunodiffusion method, an ouchterlony immunodiffusion method, a rocket immunoelectrophoresis method, an immunohistostaining method, an immunoprecipitation assay method, a complement fixation assay method, a fluorescence activated cell sorter (FACS) method, a protein chip assay method, or the like, but is not limited thereto.

In another general aspect, the present invention provides a diagnostic kit for cancer, including the composition for detecting colon cancer.

More specifically, the present invention provides a diagnostic kit for colon cancer including at least one antibody having specificity to the colon cancer marker polypeptide including proteins encoded by the polynucleotide sequence of SEQ ID NOS: 5 to 8.

In the present specification, the cancer marker polypeptide means polypeptide of which expression level is specifically changed in cells obtained from colon cancer patients or tissue of the colon cancer patient. In addition, the antibodies of the present invention may be prepared using the protein encoded by the polynucleotide sequence of SEQ ID NOS: 5 to 8 as an antigen and be polyclonal or monoclonal antibodies specific to the marker polypeptide.

In the present invention, the term "antibody" means a specific protein molecule that indicates an antigenic region. With respect to the objects of the present invention, the antibody specifically binds to a marker protein and includes all of the polyclonal antibodies, monoclonal antibodies, and recombinant antibodies.

As described above, since the colon cancer marker proteins are identified, antibody production using the colon cancer marker proteins may be easily carried out using techniques widely known in the art.

The polyclonal antibody may be produced by a method widely known in the art, which includes a method of injecting the colon cancer marker protein antigen into an animal and collecting blood samples from the animal to obtain serum containing antibodies. This polyclonal antibody may be prepared from a certain animal host, such as goats, rabbits, sheep, monkeys, horses, pigs, cows, and dogs.

The monoclonal antibody may be prepared by a method widely known in the art, such as a hybridoma method (Kohler and Milstein, European Journal of Immunology 6: 511-519, 1976), or a phage antibody library technique (Clackson et al., Nature, 352:624-628, 1991; Marks et al., J. Mol. Biol., 222: 58, 1-597, 1991). The antibody prepared by the above methods may be isolated and purified using methods such as gel electrophoresis, dialysis, salting out, ion exchange chromatography, affinity chromatography, and the like.

In addition, the antibody of the present invention may include functional fragments of antibody molecules as well as complete forms thereof having two full-length light chains and two full-length heavy chains. The functional fragments of antibody molecules refer to fragments retaining at least antigen-binding function, and include Fab, F(ab'), F(ab')2, Fv, and the like. In another general aspect, the present invention provides a diagnostic kit for colon cancer, including the composition for detecting colon cancer. Preferably, the diagnostic kit for colon cancer may be configured to include a composition, solution, or apparatus, which includes one or more kinds of different constituents suitable for analysis methods.

The diagnostic kit may be a diagnostic kit characterized by including essential elements required for performing reverse transcriptase polymerase chain reaction (RT-PCR). An RT-PCR kit includes a pair of primers specific for each marker gene. The primers are nucleotides having sequences specific to a nucleic acid sequence of each marker gene, and have a length of about 7 bp to 50 bp, more preferably about 10 bp to 30 bp. Also, the RT-PCR kit may include primers specific to a nucleic acid sequence of a control gene. The RT-PCR kit may further include test tubes or other suitable containers, reaction buffers (varying in pH and a concentration of magnesium), deoxynucleotides (dNTPs), enzymes such as Taq-polymerase and reverse transcriptase, DNAse, RNAse inhibitor, DEPC-treated water, and sterile water.

In another general aspect, the present invention relates to a diagnostic kit characterized by including essential elements required for performing a DNA chip assay. A DNA chip kit may include a base plate onto which cDNA or oligonucleotides corresponding to genes or fragments thereof, or are attached, and reagents, agents and enzymes for preparing fluorescent probes. Further, the base plate may include cDNA or oligonucleotides corresponding to a control gene or fragments thereof.

In addition, preferably, the diagnostic kit may be a diagnostic kit characterized by including essential elements required for performing ELISA. An ELISA kit includes antibodies specific to marker proteins. The antibodies are monoclonal, polyclonal or recombinant antibodies, which have high specificity and affinity to each marker protein and rarely have cross-reactivity to other proteins. Furthermore, the ELISA kit may include an antibody specific to a control protein. The ELISA kit may further include reagents capable of detecting bound antibodies, for example, a labeled secondary antibody, chromophores, enzymes (for example, enzymes capable of being conjugated with the antibody) and their substrates, or other substances capable of binding to the antibodies.

The present invention provides a method of diagnosing colon cancer, using the diagnostic composition or kit for colon cancer.

In another general aspect, there is provided a method of diagnosing colon cancer including: measuring mRNA levels in a biological sample from a patient with suspected colon cancer using primers specific to at least one gene selected from KRT5, TUBB, COL6A1, and JUP; and comparing mRNA levels of the sample from the patient with those of a normal control sample to determine an increase in mRNA levels.

The isolation of mRNA from the biological sample may be performed using a known process, and mRNA levels may be measured by various methods.

In the present invention, the term "biological sample" includes samples displaying a difference in expression levels of a colon cancer marker gene, such as tissue, cells, whole blood, serum, plasma, saliva, sputum, cerebrospinal fluid, or urine, but is not limited thereto.

Analysis methods for measuring the mRNA levels include RT-PCR, competitive RT-PCR, real-time RT-PCR, RNase protection assay (RPA), Northern blotting, DNA chip assay, and the like, but are not limited thereto.

With the detection methods, the mRNA expression level of the colon cancer marker gene in the patient with suspected colon cancer may be compared with that in a normal control, and the patient's suspected colon cancer is diagnosed by determining whether expression levels of mRNA from the colon cancer marker gene have significantly increased.

mRNA expression levels are preferably measured by the RT-PCR method or the DNA chip assay method using primers specific to the gene used as the colon cancer marker.

In the RT-PCR method, RT-PCR products are electrophoresed, and patterns and thicknesses of bands are analyzed, such that whether mRNA from a gene used as the diagnostic marker of colon cancer is expressed or not and levels of the mRNA may be confirmed. Then, the existence of colon cancer may be simply diagnosed by comparing the confirmed results with those of a control. Alternatively, in the DNA chip assay method, mRNA expression levels are measured using a DNA chip onto which the colon cancer marker genes or fragments thereof are adhered at high density to a glass-like base plate. A cDNA probe labeled with a fluorescent substance at its end or internal region is prepared using mRNA isolated from a sample, and is hybridized with the DNA chip, thereby making it possible to diagnose the existence of colon cancer.

In another general aspect, there is provided a method of diagnosing colon cancer including: measuring protein levels by allowing an antibody specific to at least one gene selected from KRT5, TUBB, COL6A1, and JUP to contact a biological sample from a patient with suspected colon cancer to form antigen-antibody complexes; and comparing protein levels of the sample from the patient with those of a normal control sample to determine an increase in protein levels.

The isolation of the protein from the biological sample may be performed using a known process, and the protein levels may be measured by various methods.

Analysis methods for measuring protein levels include the western blotting method, the ELISA method, the radioimmunoas say method, the radioimmunodiffusion method, the ouchterlony immunodiffusion method, the rocket immunoelectrophoresis method, the immunohistostaining method, the immunoprecipitation assay method, the complement fixation assay method, the FACS method, the protein chip assay method, and the like, but are not limited to thereto.

With the analysis methods, the patient with suspected colon cancer is compared with a normal control for the amount of formed antigen-antibody complexes, and the patient's suspected colon cancer is diagnosed by evaluating a significant increase in expression levels of the protein from the colon cancer marker gene.

In the present invention, the term "antigen-antibody complexes" means binding products of the colon cancer marker protein to the antibody specific thereto. The amount of the formed antigen-antibody complexes may be quantitatively determined by measuring the signal intensity of a detection label.

This detection label may be selected from a group consisting of enzymes, fluorescent substances, ligands, luminescent substances, microparticles, redox molecules, and radioactive isotopes, but is not necessarily limited thereto. In the case in which enzymes are used as the detecting label, examples of available enzymes include β-glucuronidase, β-D-glucosidase, β-D-galactosidase, urase, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphenolpyruvate decarboxylase, and β-latamase, and the like, but are not limited thereto.

Examples of the fluorescent substances include fluorescin, isothiocyanate, rhodamine, phycoerythrin, phycocyanin, allophycocyanin, o-phthaldehyde, fluorescamin, and the like, but are not limited thereto. Examples of the ligands include biotin derivatives, and the like, but are not limited to, biotin derivatives. Examples of luminescent substances include acridinium esters, luciferin, luciferase, and the like, but are not limited thereto.

Examples of the micro-particles include colloidal gold, colored latex, and the like, but are not limited thereto. Examples of the redox molecules include ferrocene, ruthenium complexes, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$, $[MO(CN)_8]^{4-}$, and the like, but are not limited thereto. Examples of the radioactive isotopes include $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, $^{186}Re$, and the like, but are not limited thereto.

Preferably, the protein expression levels may be measured by the ELISA method. Examples of the ELISA method include various ELISA methods such as a direct ELISA method using a labeled antibody recognizing an antigen attached to a solid support, an indirect ELISA using a labeled antibody recognizing a capture antibody in the antigen complexes recognizing an antigen attached to a solid support, a direct sandwich ELISA method using another labeled antibody recognizing an antigen in an antigen-antibody complex attached to a solid support, and an indirect sandwich ELISA, in which another labeled antibody recognizing an antigen in an antigen-antibody complex attached to a solid support is reacted, and then a secondary labeled antibody recognizing the another labeled antibody is used. More preferably, the protein expression levels may be detected by the sandwich ELISA method, where a sample reacts with an antibody attached to a solid support, and the resulting antigen-antibody complexes are detected by adding a labeled antibody specific to the antigen, followed by enzymatic development, or by first adding an antigen-specific antibody and then a secondary labeled antibody which binds to the antigen-specific antibody, followed by enzymatic development. The existence of colon cancer may be diagnosed by measuring the formation degree of complex of the colon cancer marker protein and the antibody.

Further, the protein expression levels are preferably measured by western blotting using at least one antibody to the colon cancer marker. Total proteins are isolated from the sample, electrophoresed to be separated according to sizes, transferred onto a polyyinylidene fluoride membrane, and reacted with an antibody. The amount of proteins produced by gene expression is determined by measuring the amount of produced antigen-antibody complexes using a labeled antibody, thereby diagnosing the incidence of colon cancer. The detection method is performed by assessing expression levels of marker genes in the control and the cells in which colon cancer occurs. mRNA or protein levels may be expressed as an absolute (e.g., μg/ml) or relative (e.g., relative intensity of signals) difference in the amount of marker proteins.

In addition, the protein expression levels are preferably measured by immunohistostaining using at least one antibody to the colon cancer marker. Normal colon epithelial tissue and cancer suspected tissue were collected and fixed, and then paraffin-embedded blocks were prepared according to a widely known method. The blocks were cut into small sections having a thickness of several um and attached to glass slides, and then were reacted with one selected from the above antibodies according to a known method. Subsequently, the unreacted antibodies were washed, and the reacted antibodies were labeled with one selected from the above mentioned detection labels and then observed under a microscope.

In addition, the protein expression levels are preferably measured using a protein chip in which at least one antibody to the colon cancer marker is arranged at a predetermined position and fixed at high density. According to the method of analyzing the sample using the protein chip, proteins are isolated from the sample, the isolated proteins are mixed with the protein chip to form antigen-antibody complexes, the formed complexes are read, and presence or expression degrees of the protein is confirmed, such that incidence of the colon cancer may be diagnosed.

Advantageous Effects

As set forth above, the present invention provides diagnostic markers for detecting metastasis and prognosis of colon cancer, thereby providing useful information for the treatment and management of colon cancer. Further, the diagnostic markers can be used for the development of colon cancer-specific anticancer agents.

DESCRIPTION OF DRAWINGS

The patent or application file contains at least one drawing executed in color. Copies of this patent or patent application publication with color drawings will be provided by the Office upon request and payment of the necessary fee.

The above and other objects, features and advantages of the present invention will become apparent from the following description of preferred embodiments given in conjunction with the accompanying drawings, in which.

MODE FOR INVENTION

Hereinafter, the present invention will be described in detail with reference to Examples and the accompanying drawings. However, the embodiment of the present invention has been disclosed for illustrative purposes, but the scopes of the present invention are not limited thereby.

Example 1

Figure 1:
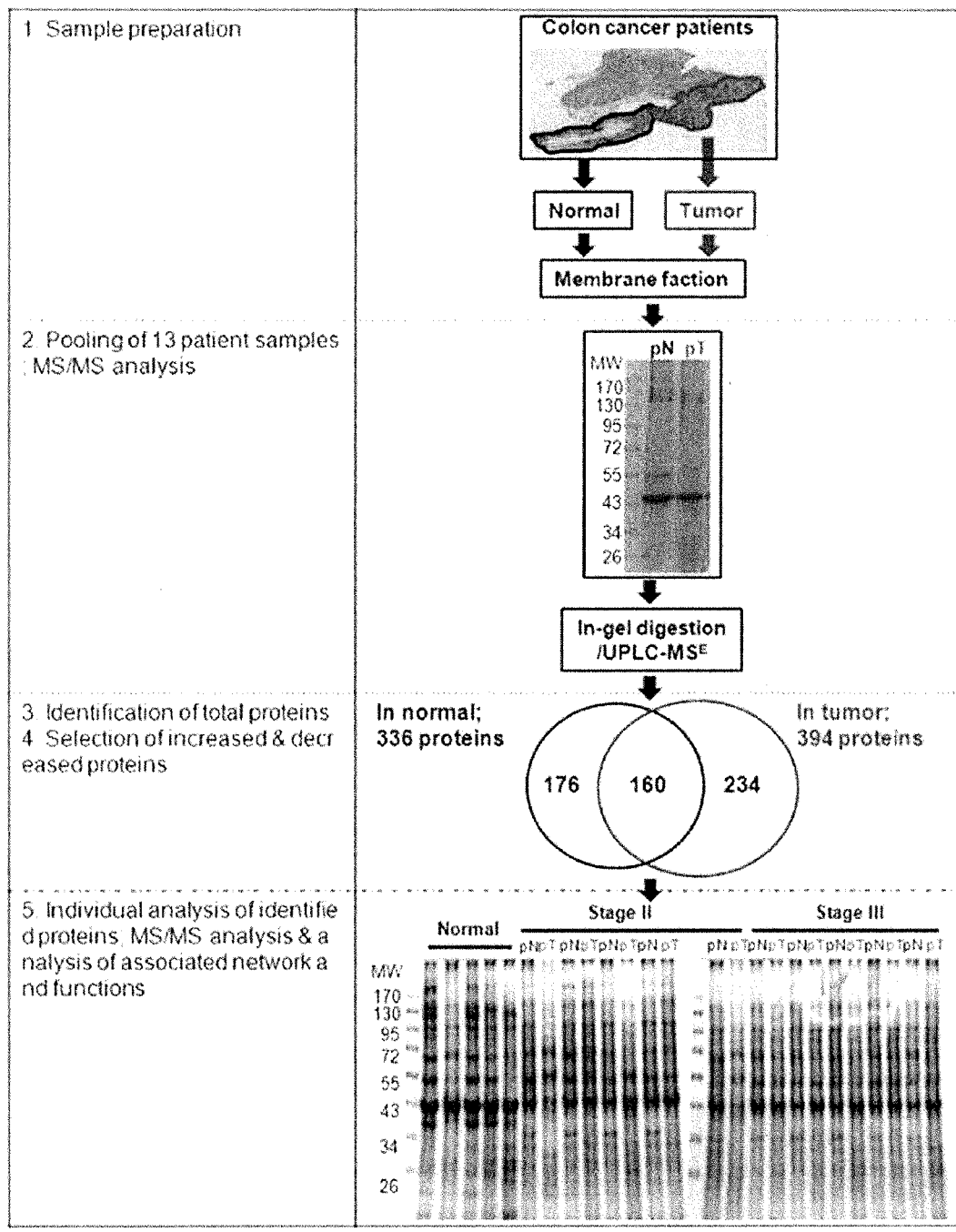
FIG. 1 is a diagram of proteomics for analyzing identification and expression change patterns of colon cancer specific proteins according to the present invention.

A method of a representative experiment according to the present invention was shown in a diagram of FIG. 1. As shown in FIG. 1, proteomics for analyzing identification and expression change patterns of colon cancer specific proteins according to the present invention is a method of accurately and finely predicting colon cancer specific expression change in a specific protein.

Cancer-specific expression information identified through the proteomics of the present invention may be applied from basic studies such as a functional study of identified proteins in vitro or in vivo, or the like, to clinical studies such as development of bio-marker diagnostic antibodies, or the like.

(1) Proteomics Analysis

Proteomics was performed for identifying colon cancer specific expression proteins and selecting proteins having expression changes.

Nano-UPLC-$MS^E$ proteomics was performed in order to identify proteins showing an expression change between normal tissue and cancer tissue and analyze sequences thereof. In the experimental method, in order to confirm overall expression changes in protein groups and quantitative analysis in various cancer samples, each of colon cancer patient samples were dissolved, and then only membrane fractions were isolated. The isolated sample was isolated by 8% gel. After protein patterns were compared with each other through Coomassie staining, the isolated sample was cut into fragments having an adequate size, and in-gel tryptic digestion was performed on each of the gel fragments. The peptides isolated and identified as described above were recovered, and relative quantity analysis (ultraperformance liquid column, high/low collision energy MS: nano-UPLC-$MS^E$), which is a precise shotgun proteomics, was performed on the recovered polypeptides, thereby microsequencing the peptides. Based on 5527 peptides selected through the proteomics, totally, 168 normal tissues and 225 cancer tissues were identified using MASCOT (version 2.1) database (DB) search engine (Matrix Science, London, UK) and IPI_human_version 2.33 (ebi.ac.uk). Proteins having changing rates in the expression degree were 20% were distinguished by predicting protein expression changes between the normal tissue and the cancer tissue using relative quantification of the proteomics among 83 proteins that are identified in the normal tissue and the cancer tissue. Among the proteins, information and quantitative information of proteins predicted that the proteins was related to colon cancer was shown in Table 1.

TABLE 1

Proteins having expression changes between normal tissue and cancer tissue of a colon cancer patient

| IPI No. | Protein Name | Gene Symbol | Score (PLGS) | CT:CN log(e)ratio | CT:CN Ratio | Sequence Coverage(%) |
|---|---|---|---|---|---|---|
| IPI00009867 | Keratin, type II cytoskeletal 5 | KRT5 | 316.2 | 0.21 | 1.23 | 26.1 |
| IPI00011654 | Tubulin, beta | TUBB | 404.67 | 1.45 | 4.26 | 37.5 |

TABLE 1-continued

Proteins having expression changes between normal tissue and cancer tissue of a colon cancer patient

| IPI No. | Protein Name | Gene Symbol | Score (PLGS) | CT:CN log(e)ratio | CT:CN Ratio | Sequence Coverage(%) |
|---|---|---|---|---|---|---|
| IPI00291136 | Collagen, type VI, alpha 1 | COL6A1 | 1667.15 | −1.55 | 0.21 | 72.3 |
| IPI00554711 | Junction plakoglobin | JUP | 384.53 | −0.52 | 0.59 | 50.1 |

(2) Analysis of Functional Relationships Between Proteins Showing Cancer-Specific Expression Changes in a Cell In order to research into expression changes of colon cancer specific target proteins selected in Example 1 and functional relationships between the proteins in a cell, bioinformatics analysis was performed. Whether protein groups isolated and identified through the proteomics is increased or not was confirmed, and relationships between the increased proteins in each of the normal tissues and the cancer tissues were determined through ingenuity pathway analysis (IPA) program (Ingenuity Systems Inc., ingenuity.com). An intracellular network of the protein groups of which relationships were confirmed was analyzed, influences on intracellular signaling were predicted through the program analysis, and functions of the target proteins were analyzed, such that the results were shown in the following Table 2 and FIGS. 2 and 3.

TABLE 2

Intracellular relationship according to functions between expression-changed proteins through ingenuity analysis

Figure 2:
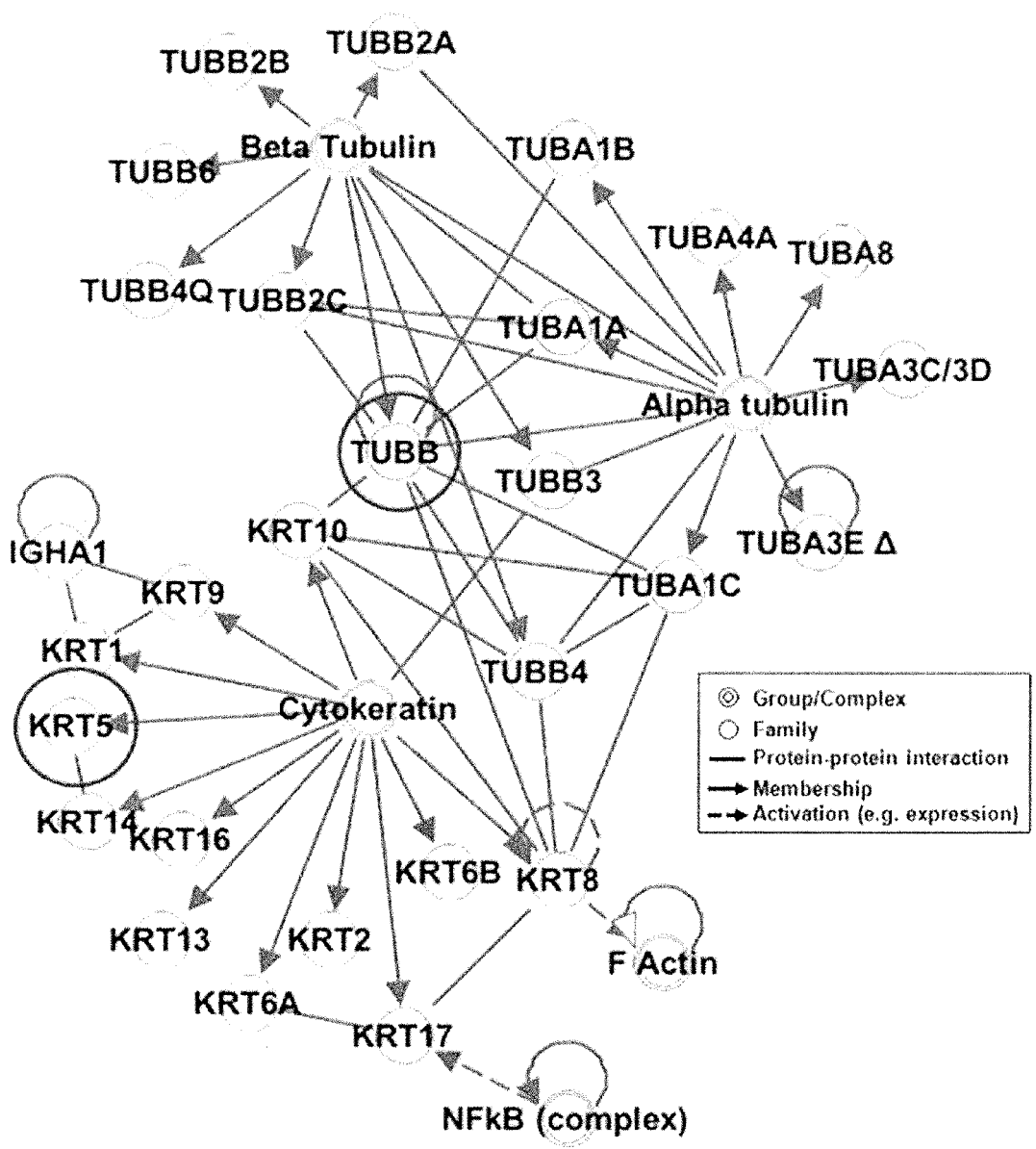
FIG. 2 is a diagram analyzing relationships between intracellular functions with respect to protein groups related to colon cancer and showing a network of the protein groups related to colon cancer.
Figure 3:
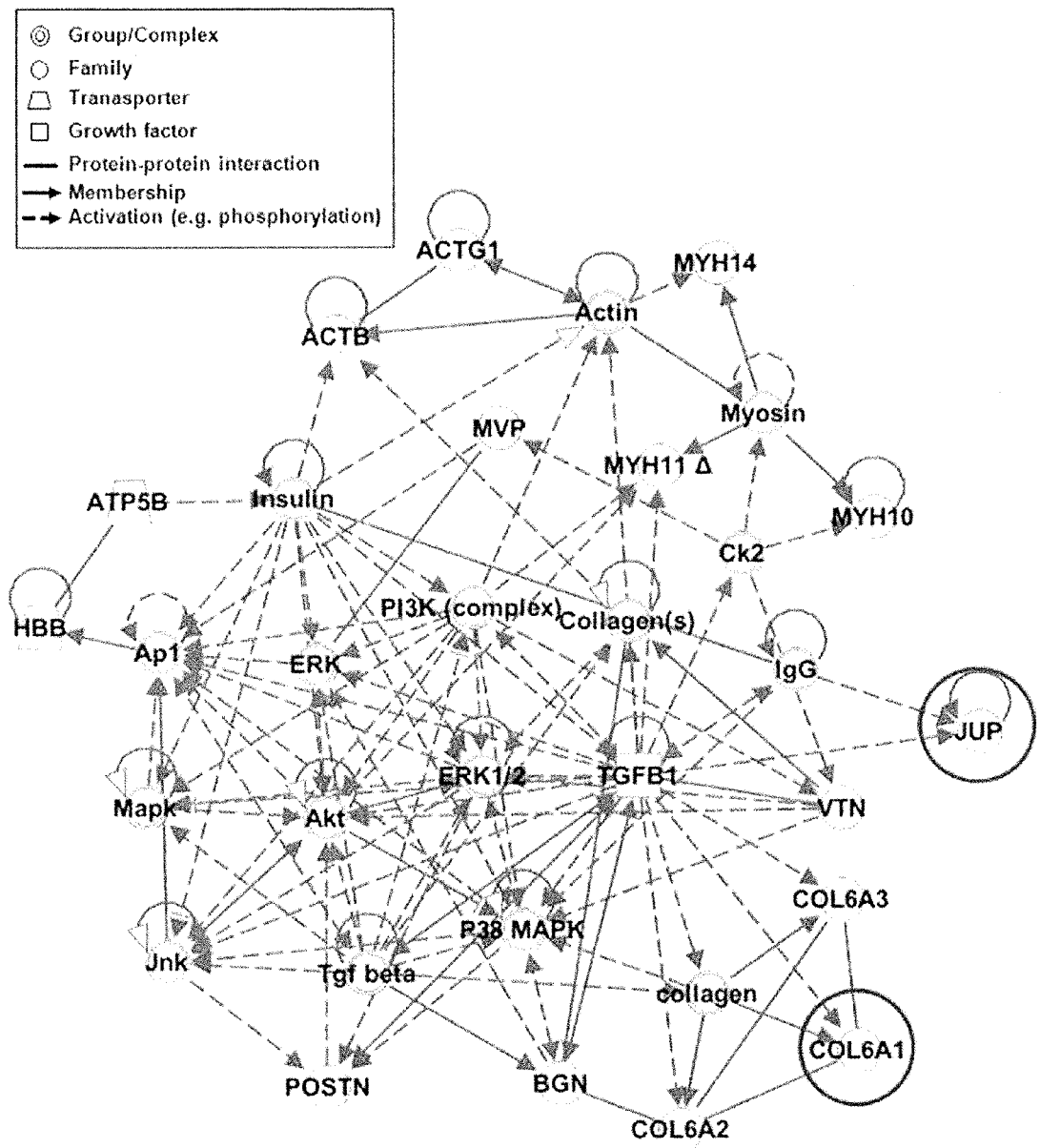
FIG. 3 is a diagram analyzing functional relationships in cell with respect to protein groups related to colon cancer and showing a network of the protein groups related to genetic disorder, skeletal and muscular disorder, and cardiac damage.

| Network | Molecules | |
|---|---|---|
| Cancer, Reproductive System Disease, Cardiac Inflammation | KRT5, TUBB | FIG. 2 |
| Genetic Disorder, Skeletal and Muscular Disorders, Cardiac Damage | COL6A1, JUP | FIG. 3 |
| 1. Diseases and Disorders | | |
| Dermatological Diseases and Conditions, Reproductive System Disease | COL6A1, JUP, KRT5 | |
| Cancer | COL6A1, JUP, KRT5, TUBB | |
| Cardiovascular Disease | COL6A1, JUP | |
| Infectious Disease | TUBB | |

TABLE 2-continued

Intracellular relationship according to functions between expression-changed proteins through ingenuity analysis

| Network | Molecules |
|---|---|
| 2. Molecular and Cellular Functions | |
| Cellular Assembly and Organization, Cellular Function and Maintenance | TUBB |
| Cell Morphology, Cell-To-Cell Signaling and Interaction | JUP |
| 3. Physiological System Development and Function | |
| Hair and Skin Development and Function, Organ Development | JUP, KRT5 |
| Cardiovascular System Development and Function, Tissue Development | JUP |

As shown in Table 2, it was analyzed that the colon cancer specific target proteins selected in Example 1 has many relationships particularly with induction of various diseases and is significantly involved in functions capable of changing intracellular environments.

Experimental Example

A western blotting method, which is a method of finding only the desired protein (antigen) in protein mixtures using antibody reacting with an antigenic epitope, was performed in order to confirm proteomics results with expression patterns of proteins predicted that the protein will be differently expressed in colon cancer patients and normal persons based on analysis results of the proteomics of the above Example.

(1) Preparation of Antibodies Using Antigens of Colon Cancer-Specific Protein

Peptides of the 4 proteins KRT5, TUBB, COL6A1, and JUP firstly selected in Example 1 were used as antigens, thereby preparing the antibodies.

Information of the four selected proteins is as follows.

TABLE 3

| Peptide | SEQ ID NO: | Amino acid sequence | SEQ ID NO: | Base sequence |
|---|---|---|---|---|
| KRT5 | 1 | NKYEDEINKRT TAEN | 5 | aacaagtatgaggatgaaatcaacaagcgtaccactgct gagaat |
| TUBB | 2 | DFGEEAEEEA | 6 | gatttcggtgaggaggccgaagaggaggcc |
| COL6A1 | 3 | CSFECQPARG PPGLR | 7 | tgctccttcgaatgccagcctgcaagaggacctccgggg ctccgg |
| JUP | 4 | FRISEDKNPDY RKRV | 8 | ttccgcatctccgaggacaagaacccagactaccggaa gcgcgtg |

The peptides were injected into mice together with Freund's adjuvant (Sigma Aldrich, F5506), followed by blood sampling, and then western blotting was performed in order to confirm whether expression changes in each of the proteins coincide with proteomic data or not. Here, in order to predict accurate expression changes, experiments were performed using colon tissue sample of a normal person as a control.

Figure 4:
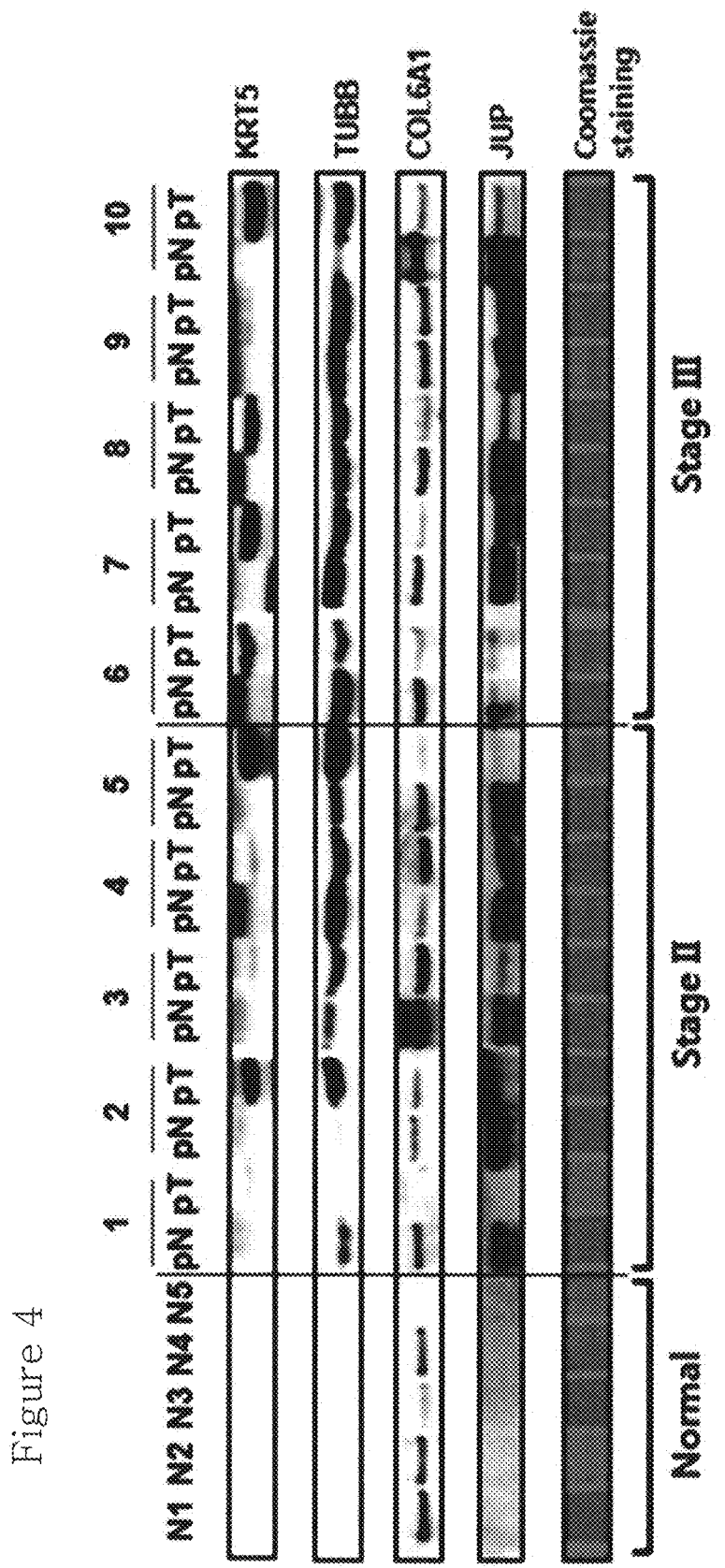
FIG. 4 is a photograph showing a change in protein expression in a normal person and a colon cancer patient using an antibody specifically binding to polypeptide according to the present invention.
Figure 5:
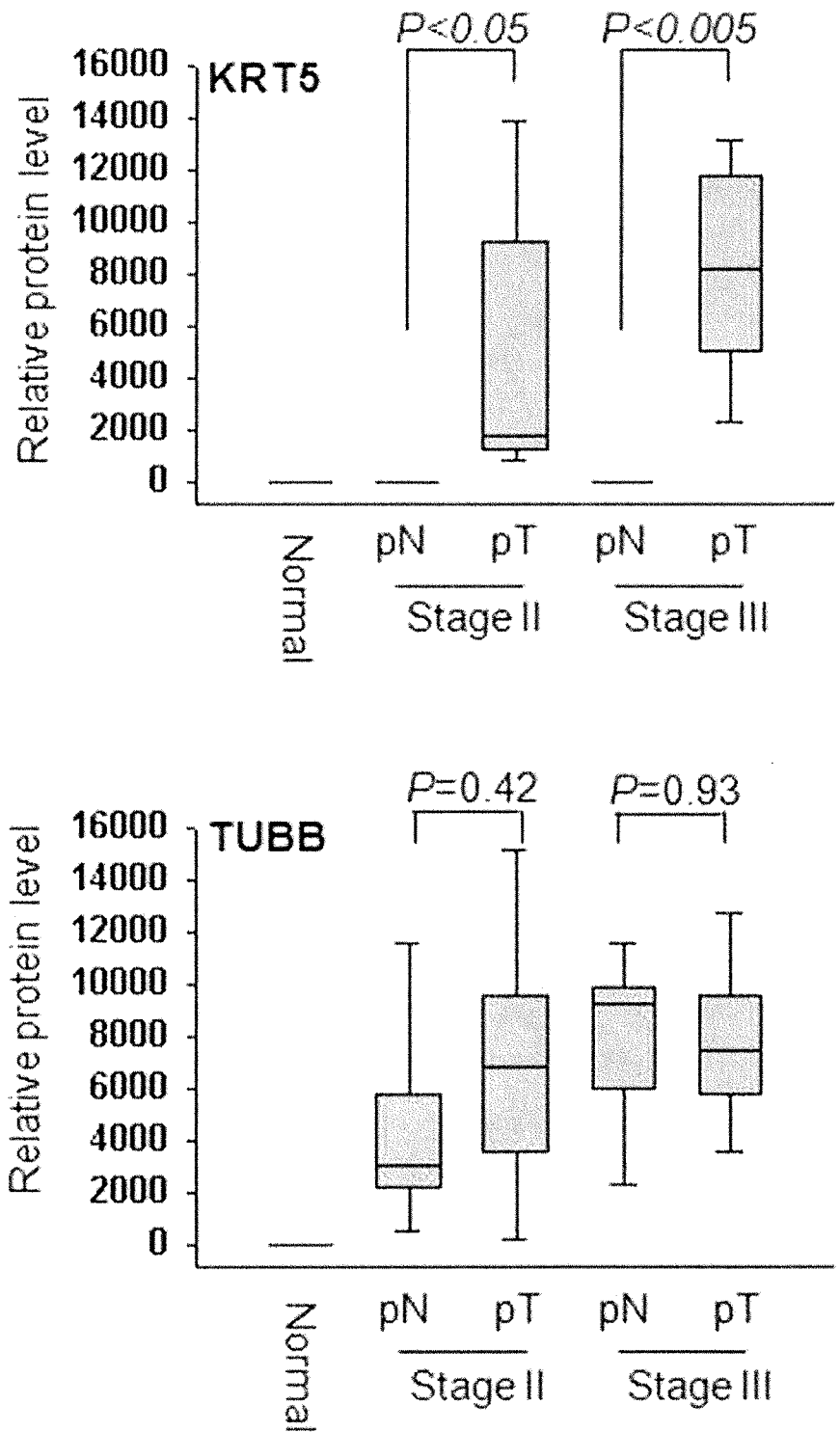
FIG. 5 is a graph showing results obtained by analyzing expression degrees of KRT5 and TUBB of FIG. 4, wherein N: colon tissue of normal person, pN: normal tissue of colon cancer patient, pT: cancer tissue of colon cancer patient.
Figure 6:
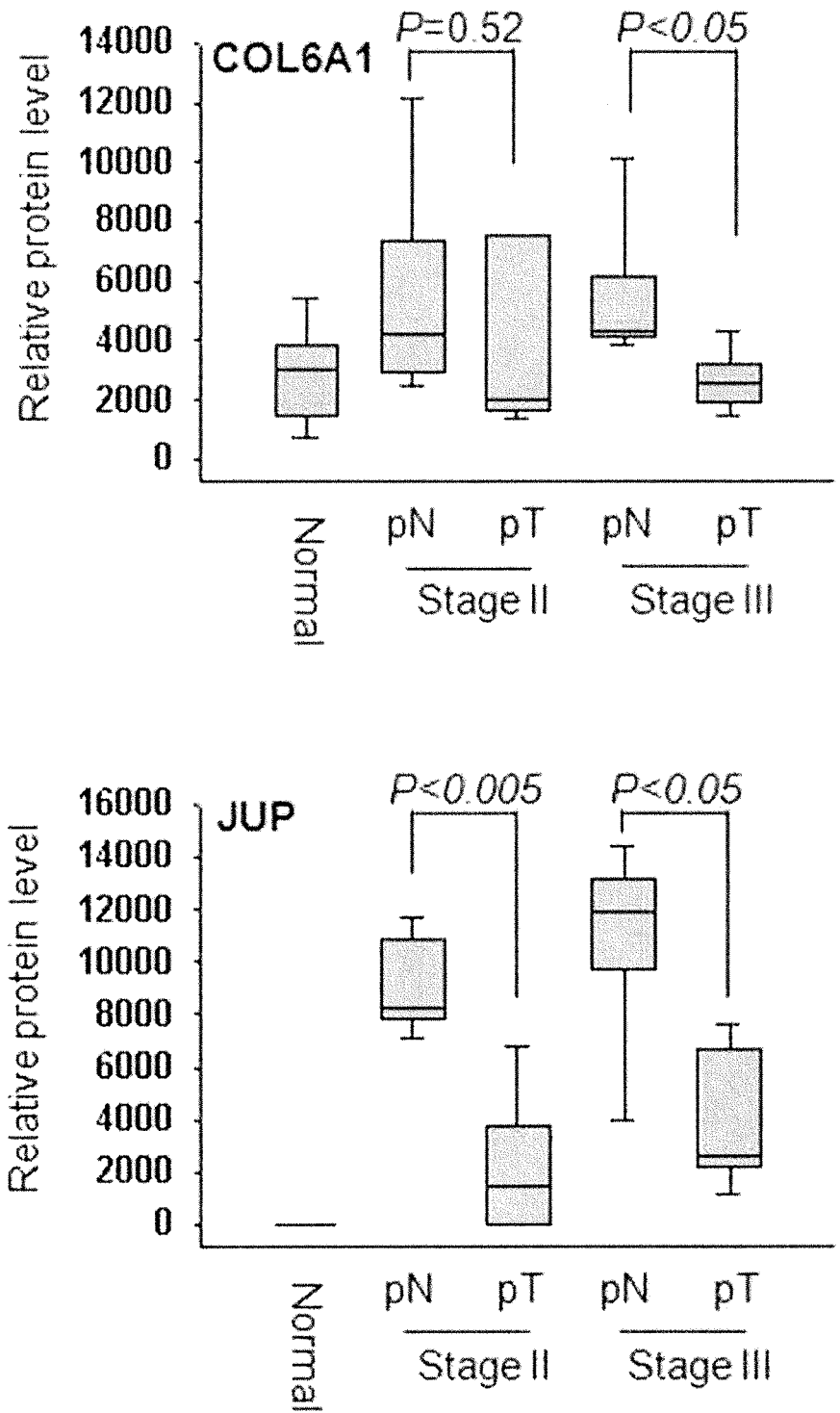
FIG. 6 is a graph showing results obtained by analyzing expression degrees of COL6A1 and JUP of FIG. 4, wherein N: colon tissue of normal person, pN: normal tissue of colon cancer patient, pT: cancer tissue of colon cancer patient.

As a result, it may be confirmed that the same expression patterns were shown as those of proteomics quantitative analysis as shown in FIGS. 4 to 6.

Through the above results, it may be confirmed that colon cancer may be diagnosed early using a content of four tissue proteins expressed differently from normal persons in tissue and in the case in which four polypeptides are used as a marker for detecting colon cancer, interpretation of the results is rapid and accurate and diagnosis is easy for early diagnosis of colon cancer.

SEQUENCE LIST TEXT

SEQ ID NO: 1 is an amino acid sequence of KRT2 peptide.
SEQ ID NO: 2 is an amino acid sequence of TUBB peptide.
SEQ ID NO: 3 is an amino acid sequence of COL6A1 peptide.
SEQ ID NO: 4 is an amino acid sequence of JUP peptide.
SEQ ID NO: 5 is a base sequence of KRT2 peptide.
SEQ ID NO: 6 is a base sequence of TUBB peptide.
SEQ ID NO: 7 is a base sequence of COL6A1 peptide.
SEQ ID NO: 8 is a base sequence of JUP peptide.

The invention claimed is:

1. A composition capable of detecting a colon cancer, said composition comprising the following antibodies (a)-(d):
   (a) an antibody specifically binding a polypeptide of SEQ ID NO: 1;
   (b) an antibody specifically binding a polypeptide of SEQ ID NO: 2;
   (c) an antibody specifically binding a polypeptide of SEQ ID NO: 3; and
   (d) an antibody specifically binding a polypeptide of SEQ ID NO: 4,
   wherein said composition is used to detect a colon cancer.

2. A kit for detecting a colon cancer comprising the composition of claim 1.

3. The kit of claim 2, wherein the kit is a protein chip kit.

4. The composition of claim 1, wherein the antibodies are bound to a detectable label.

5. A method for detecting a colon cancer in a subject, comprising contacting a sample of the subject with the composition of claim 1 and detecting binding of the polypeptides of SEQ ID NOS: 1-4 in the sample to the antibodies of the composition of claim 4 wherein, differences in expression level of the polypeptides of SEQ ID NOS: 1-4 in the sample, measured as the binding, compared to expression level of the polypeptides of SEQ ID NOS: 1-4 in normal control sample, indicate an existence of a colon cancer in the subject.

* * * * *